United States Patent [19]

Maini

[11] Patent Number: 4,890,482
[45] Date of Patent: Jan. 2, 1990

[54] METHOD AND APPARATUS FOR MEASURING FLUID VISCOSITY

[75] Inventor: Brij B. Maini, Calgary, Canada

[73] Assignee: Alberta Oil Sands Technology and Research Authority, Edmonton, Canada

[21] Appl. No.: 234,759

[22] Filed: Aug. 22, 1988

[51] Int. Cl.$^4$ .......................................... G01N 11/04
[52] U.S. Cl. ...................................................... 73/55
[58] Field of Search .................................. 73/54, 55, 56

[56] References Cited

U.S. PATENT DOCUMENTS

| | | | |
|---|---|---|---|
| 3,548,638 | 12/1970 | Uchida et al. | 73/55 |
| 3,930,402 | 1/1976 | Detmar et al. | 73/55 |
| 4,478,071 | 10/1984 | Lecacheux et al. | 73/55 |
| 4,566,314 | 1/1986 | Thurston | 73/55 |
| 4,723,442 | 2/1988 | Manning et al. | 73/55 |

Primary Examiner—John Chapman
Assistant Examiner—Michele Simons
Attorney, Agent, or Firm—Ernest Peter Johnson

[57] ABSTRACT

A transient flow capillary viscometer is provided for establishing a measure of the viscosity of a highly viscous test fluid. More particularly, a capillary tube filled with the test fluid is provided. The viscometer relies upon inducing a step change in the differential pressure across the ends of the capillary tube, which causes the fluid to flow therein. The resultant decrease in pressure drop as a function of time, i.e. the half-life of pressure decay, is monitored and provides an approximate measure indicative of the viscosity of the fluid.

6 Claims, 5 Drawing Sheets

METHOD AND APPARATUS FOR MEASURING FLUID VISCOSITY

FIELD OF THE INVENTION

The invention relates to viscometers. More specifically, it relates to a transient flow capillary tube viscometer.

BACKGROUND OF THE INVENTION

Accurate measurements of fluid viscosities are important in many industries. In the oil and gas industry, for example, it is often necessary to obtain accurate measurements of the viscosity of the liquid hydrocarbons found in a subterranean formation. Hydrocarbon liquids found at some of the shallower depths beneath the surface of the earth can have viscosities ranging up to a million centipoise (mPa.s). Extraction of such viscous oils from the formation usually involves production techniques which rely upon lowering the viscosity of the hydrocarbons. In order to design such production techniques, it is necessary to measure oil viscosity at varying temperatures and pressures which approximate to the range of formation conditions.

Capillary viscometers of the types disclosed in U.S. Pat. No. 3,081,621 issued to N. A. De Bruyne; No. 3,116,630 issued to J. J. Piros; and No. 3,375,704 issued to B. T. Thompson, Jr. et al., may be utilized to measure the viscosity of a fluid. These devices are functional to measure the viscosity of the fluid flowing through the capillary by measuring the pressure drop across the capillary under steady-state flow conditions at a known flow rate.

In a variation of this technique, viscosity may be determined by maintaining a constant pressure drop across the capillary and measuring the time required for a predetermined volume of fluid to flow therethrough. Exemplary of such devices are those shown in U.S. Pat. No. 4,302,965 issued to T. W. Johnson et. al.; No. 3,699,804 issued to H. U. Gassmann et. al. and No. 3,353,403 issued to F. H. Deily et. al.

Alternative arrangements involve the use of two or more capillaries in series or parallel. Such viscometers are described, for example, in U.S. Pat. No. 3,808,877 issued to D. E. Blair; No. 3,798,960 issued to J. R. Glass; No. 4,578,990 issued to S. D. Abbott et. al. and No. 2,934,944 issued to D. Eolkin.

All of the viscometers disclosed in the above-mentioned patents rely on the Hagen-Poiseuille law, which states:

$$Q = \frac{\pi \Delta p R^4}{8 \mu L}$$

where:
$\mu$ is the viscosity of the fluid flowing through the capillary tube;
$\Delta p$ is the pressure head;
$R$ is the capillary tube radius;
$L$ is the length of the capillary tube; and
$Q$ is the rate of fluid flow through the capillary tube.

It will be appreciated that the Hagen-Poiseuille law is strictly valid only when the following conditions are satisfied, namely:
the flow is laminar;
the fluid density is constant (i.e. "incompressible flow");
the flow rate is constant (i.e. "steady state");
the fluid behaves as a continuum;
no slip exists at the wall; and
the end effects are negligible.

In summary, therefore, these prior art methods for measuring viscosity involve varying only a single parameter in the Hagen-Poiseuille equation. From this parameter the viscosity measure is derived. This variable may be either the pressure drop across the capillary, the flow rate, or the time required for a given volume of fluid to pass through the capillary. Such methods thus require provision of a means for generating a predetermined constant flow rate (usually a constant rate pump), or means for maintaining constant differential pressure across the capillary (usually constant fluid head).

Additionally, to ensure the integrity of the equation, it is necessary to achieve steady state flow conditions.

Whilst such methods are well adapted for many fluids, they are not suitable for highly viscous heavy oils and the like. The problems inherent with these methods are associated with difficulties in pumping viscous fluids and in measuring flow rate at high pressures and elevated temperatures. Additionally, the attainment of steady state flow conditions, which may take several hours, is time-consuming. Another disadvantage is that relatively large volumes of test fluids may be required.

Rotational or vibrational viscometers, which may provide an alternative, are expensive and difficult to use at high temperatures and pressures.

There exists therefore the need for a method and apparatus suitable for determining the viscosity of highly viscous fluids at elevated temperature and pressure having the characteristics of:
providing a rapid indicia of viscosity;
being adapted for transient flow conditions, thereby eliminating the requirement for 'steady state' conditions and hence for provision of means for generating constant flow rate or means for maintaining a constant differential pressure across the capillary; and
reducing the requirement for large volumes of test fluid.

By 'transient' flow conditions is meant that as a pressure differential between two points progressively decreases, or decays, there is a concomitantly diminishing flow rate associated therewith. Stated otherwise, there is more than one parameter, used in the Hagen-Poiseuille equation, which is varying.

SUMMARY OF THE INVENTION

The viscometer of the present invention involves:
a capillary tube having upstream and downstream ends and being filled with the test fluid;
means for keeping the capillary tube filled with test fluid during testing;
an upstream pressure vessel containing a slightly compressible fluid, such as water, said upstream vessel preferably being connected to the upstream end of the capillary tube by the means for keeping the tube filled with test fluid;
means, such as a pump, for increasing the pressure within the upstream vessel by compressing the contained fluid;
means, such as a valve, for controlling the flow of liquid and the application of pressure from the upstream vessel through the connecting means to the capillary tube, whereby a pulse of pressure may be applied to the upstream end of the capillary tube by opening the valve;

means, such as a gas-filled downstream pressure vessel connected by a conduit to the downstream end of the capillary tube, for receiving the fluid exiting the capillary tube and maintaining a substantially constant elevated pressure at the outlet of the capillary tube;

preferably, means, such as an oven, enclosing the capillary tube, for heating the test fluid in the tube;

means, such as a pressure transducer, connected to progressively measure the changing pressure differential across the capillary tube during the transient flow of the test fluid; and means, such as chart recorder, for recording the magnitude of the diminishing differential pressure, either continuously or periodically at known intervals of the time, during the period in which most of the transient flow takes place.

In operation, the interconnected system is pressurized to about the desired elevated test end pressure and the test fluid is heated to the test temperature. Then the fluid in the upstream vessel is further pressurized with the control valve closed, to provide the desired elevated pressure increment relaive to the test end pressure. The valve is then opened to create a sudden pressure drop across the capillary tube (which we refer to as 'inducing a pressure drop in a pulsed manner'). A small amount of test fluid flows at a diminishing rate and under a diminishing pressure drop through the capillary tube as the compressed fluid in the front end of the system expands. Eventually the flow ceases when the pressure is equalized across the system. The pressure transducer and chart recorder are operative to measure the diminishing pressure differential as a function of or with time.

In this situation, the flow never becomes independent of time (i.e. steady state is not reached). Thus the Hagen-Poiseuille law cannot be applied in a strict sense. However we have found that the Hagen-Poiseuille law can be used for an approximate analysis of the flow and the resulting expression for the rate of decay of the pressure difference across the capillary tube can be used to get values indicative of viscosity which are close enough for practical use.

More particularly, by applying the Hagen-Poiseuille law, the rate of flow through the capillary tube can be expressed as:

$$Q = \frac{\pi(Pu - Pd)R^4}{8\mu L} \quad (1)$$

where,
Q is the flow rate through the capillary tube;
R is the radius of the capillary tube;
L is the length of the capillary tube;
Pu is the pressure in the upstream vessel;
Pd is the pressure in the downstream vessel; and
$\mu$ is the viscosity of the fluid filling the capillary tube.

The rate of flow through the capillary tube is equal to the rate of change of the volume of the fluid which initially filled the upstream vessel. This rate is determined by the volume of the upstream vessel, the rate of change of pressure in the upstream vessel and the compressibility of the fluid contained in the upstream vessel. Using the defining equation for compressibility, the rate of change of the volume of fluid initially in the upstream vessel can be expressed as:

$$\frac{dv}{dt} = -CV\frac{dPu}{dt} \quad (2)$$

where,
C is the compressibility of the liquid in the upstream vessel;
V is the volume of the liquid originally in the upstream vessel;
t is the time; and
Pu is the pressure in the upstream vessel.

Since the pressure change involved is small and the compressibility of the fluid in the upstream vessel is also small, for practical purposes the volume V remains substantially equal to the volume of the upstream vessel. Equating the rate of fluid expansion to the rate of flow through the capillary tube, one obtains the following expression for rate of change of the pressure difference between the two vessels:

$$\frac{d(Pu - Pd)}{dt} = \frac{-\pi(Pu - Pd)R^4}{8C\mu VL} \quad (3)$$

This equation can be integrated to obtain:

$$\ln \frac{\Delta P(t)}{\Delta P(t = o)} = -\frac{\pi R^4}{8\mu\ CVL} t \quad (4)$$

where,
$\Delta P(t) = (Pu - Pd)$ at time t, which is the differential pressure driving the flow;
$\Delta P(t = o) = (Pu - Pd)$ at time zero;

The time required for the differential pressure to decline to, for example, one-half of its existing value (half life) is given by:

$$t_{1/2} = \frac{8\mu CVL}{\pi R^4} \ln 2 \quad (5)$$

The value of this half life is therefore independent of the starting value of differential pressure and, when values of C, V, L and R are fixed, it is directly proportional to the viscosity of the test fluid. Thus, by determining the value of, for example, the half life of pressure decay, a value indicative of viscosity can be determined by the following equation:

$$\mu = Kt_{1/2} \quad (6)$$

The constant of proportionality, K, can be determined by:

$$K = \frac{\pi R^4}{8CVL \ln 2} \quad (7)$$

In summary then, a transient flow capillary viscometer is provided for measuring the viscosity of a test fluid filling a capillary tube. The viscometer is adapted to induce a step change or pulse in pressure differential across the capillary tube, thereby causing the test fluid to flow. By measuring the resultant diminishing pressure differential as a function of time (or decay), information is obtained from which a measure approximately and usefully indicative of viscosity may be derived.

The present invention differs from the prior art in several features which provide substantial advantages.

The most important distinction from the prior art lies in the use of non-steady state flow conditions for viscosity measurements. In this invention both the applied pressure head and the rate of flow through the capillary change continuously during the measurement of viscosity. Although, the Hagen-Poiseuille law is theoretically not applicable for describing the flow under such conditions, we have discovered that it can be applied in an approximate sense to obtain results which are of practical use. The second distinction lies in the use of compressibility of a second fluid confined in a pressure vessel to drive the test fluid through the capillary tube. Yet another distinction lies in the experimentally determined variable which serves as the measure of the viscosity of the test fluid. The present invention preferably uses the half life of decay of pressure difference between two pressure vessels connected by the capillary as the measure of viscosity. The value of half life is not affected by the accuracy of the differential pressure transducer as long as the transducer response remains linear with pressure.

In one broad aspect of the invention, there is provided a transient flow capillary viscometer for establishing a measure of the viscosity of a test fluid comprising: a capillary tube having upstream and downstream ends; first means, communicating with the downstream end of the capillary tube, for receiving fluid exiting, the capillary tube and maintaining a substantially constant elevated pressure at said end; second means, communicating with the upstream end of the capillary tube, for maintaining the tube filled with test fluid during testing and inducing, in a pulsed manner, a pressure differential across the tube whereby test fluid may be caused to flow therethrough at a diminishing rate under a diminishing pressure differential; and third means for monitoring the thus generated diminishing pressure differential as a function of time to obtain information which may be used to calculate a measure indicative of the viscosity of the test fluid.

In another broad aspect of the invention there is provided a method for determining a measure indicative of the viscosity of a test fluid, comprising: providing a capillary tube filled with test fluid and means for keeping the capillary tube filled with test fluid during testing; maintaining a substantially constant elevated pressure at the downstream end of the capillary tube while enabling test fluid to exit from the downstream end of the capillary tube; applying, at the upstream end of the capillary tube, a a pulse of pressure greater than the downstream end pressure to thereby induce a pressure differential across the capillary tube and cause the test fluid to flow through the capillary tube at a diminishing rate under a diminishing pressure differential; and monitoring the diminishing pressure differential across the capillary tube as a function of time to thereby obtain information which may be used to calculate a measure indicative of the viscosity of the test fluid.

DESCRIPTION OF THE PREFERRED EMBODIMENT

Figure 1:
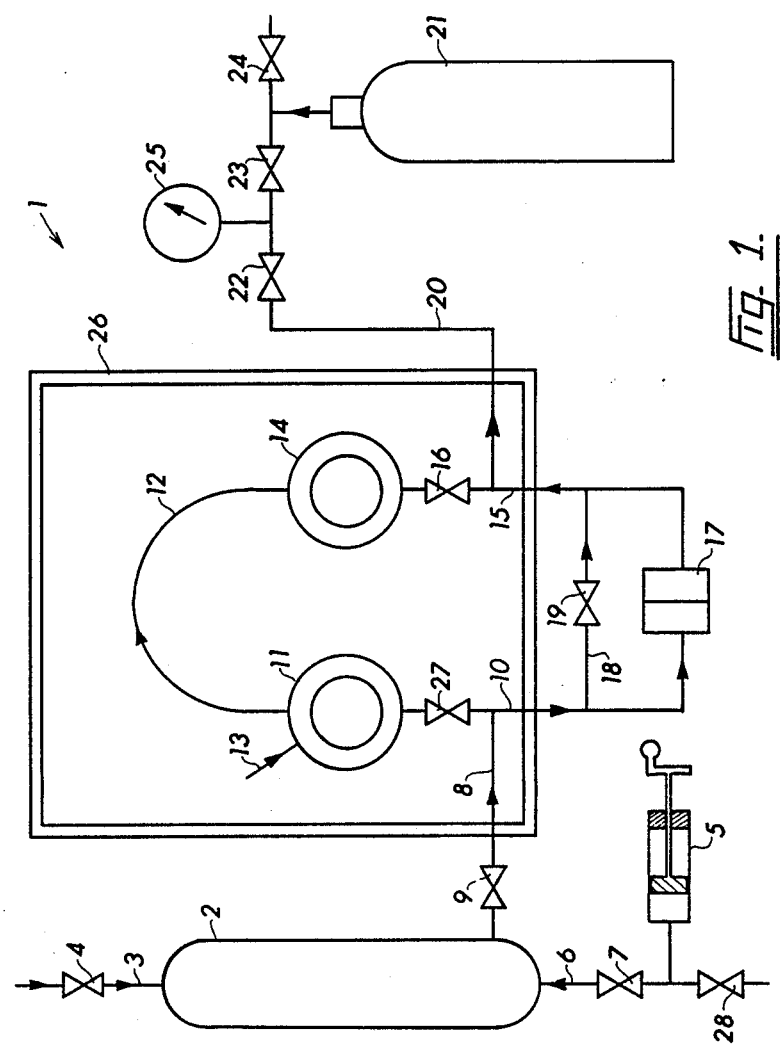
FIG. 1 is a schematic depicting a preferred embodiment of a transient flow capillary viscometer.

The viscometer 1 comprises a first pressure vessel 2 having an inlet conduit 3 controlled by a valve 4. A piston pump 5, connected to a source (not shown) of compressible liquid (e.g. water), is connected to the vessel 2 by a conduit 6 which is controlled by a valve 7. An outlet conduit 8, controlled by a valve 9, leads from the vessel 2. When actuated, the piston pump 5 is adapted to compress the liquid filling the vessel 2 when the valve 7 is open and the valve 9 is closed. Thus actuation of the pump 5 induces a pressure increase in the vessel 2.

The outlet conduit 8 from the vessel 2 connects with a conduit 10. At one end, this conduit 10 connects with a small second pressure vessel 11. The vessel 11 is connected to the upstream end of a capillary tube 12. Vessel 11 functions to provide a reservoir of test fluid, introduced through conduit 13, for keeping the capillary tube 12 filled during testing. A small fourth pressure vessel 14 connects with the downstream end of the capillary tube 12. An outlet conduit 15 leads from the vessel 14 and is controlled by a valve 16.

The conduits 10, 15 connect with an electronic pressure transducer 17 adapted to monitor pressure differential across the capillary tube 12.

A conduit 18, controlled by a valve 19, connects the conduits 10, 15 for bypassing the transducer 17 when required.

A conduit 20 connects conduit 15 with a third pressure vessel 21 filled with compressed gas, typically nitrogen. Valves 22, 23, 24 control conduit 20. A pressure gauge 25 monitors the pressure in conduit 20.

It will be appreciated that other means, such as a pressure regulator, could be used to maintain a constant pressure at the downstream end of the capillary tube.

The relatively small vessels 11, 14 and the capillary tube 12 are positioned within a temperature-controlled oven 26. Thus the test fluid may be quickly heated to the desired test temperature.

The pressure in vessel 21 is the "downstream" or final test pressure. The viscometer is particularly adapted for testing the viscosity of heavy oil at conditions approximating those expected in a subterranean reservoir. So one would conduct the tests at elevated temperatures and pressures.

At the start of the measurement the capillary tube 2 is filled with the test fluid, as are portions of vessels 11 and 14.

The upstream pressure vessel 11, piston pump 5 and the remainder of vessels 11 and 14 not containing test fluid are all filled with a slightly compressible fluid which is immiscible with the test fluid. A typical fluid is water. Similarly, all the conduits and valves are filled with the immiscible fluid. As stated earlier, pressure vessel 21 is filled with compressed gas at the pressure at which the measurements are to be carried out.

At the start of the test, valves 27, 23, 4, 28 and 24 are kept closed. The remaining valves are maintained in the open position. Valve 23 is then opened to equalize the pressure throughout the system.

The oven 26 is heated to the test temperature until thermal equilibrium is reached.

Valve 22 is then closed. The fluid pressure in vessel 2 is increased by a small increment (typically 5 psi) by actuating the piston pump 5.

The value of this step change in pressure is monitored by means of the pressure transducer 17. Valve 27 is then opened to permit the test fluid to flow through the capillary tube 12. The pressure transducer 17 continues to monitor the subsequent gradual decrease in pressure differential as the fluid flows through the capillary tube 12 as a function of time. This is referred to as the pressure decay.

The viscosity of the test fluid is derived utilizing an analysis of the transient pressure response in conjunction with the theoretical basis given hereinabove.

EXAMPLE

The following example is included to demonstrate the operability of the transient flow viscometer described herein for determining the viscosity of a heavy oil at different temperatures and at a fixed pressure.

More particularly, a capillary tube 12 having a length of 1 m, an OD of 1/16", and an ID of 0.0195" was used. The tube 2 was made of stainless steel tubing.

The vessels 11 and 14 comprised stainless steel pressure vessels each equipped with a glass window. The volumetric capacity of each of the vessels 11, 14 was approximately 10 cc.

The vessel 2 consisted of a stainless steel pressure vessel of 2 liter capacity.

The vessel 21 was a compressed nitrogen cylinder having a capacity of approximately 20 liters.

The pressure transducer 17 was a Model #DP215 supplied by Validyne Engineering Corporation, Northridge, Calif.

The oven 26 was a horizontal air flow convection oven Model POM7-136C-3, supplied by Blue M Electric Company, Blue Island, Ill., U.S.A.

The piston pump 5 consisted of a 10 cc hand-operated syringe pump.

The transducer response was recorded on a chart recorder.

The pressure gauge 25 was of the Bourden tube type. All connecting conduits were ¼" OD, made of stainless steel. The valves were Autoclave Engineers series 10 V type in ¼" size.

In operation, before conducting viscosity measurements, the capillary tube 12 and the vessels 11 and 14 were cleaned with solvents and dried. All vessels and tubing except 11, 21 and 14 and the capillary tube 12 were filled with degassed, distilled water. The pressure in vessel 21, which was filled with compressed nitrogen, was maintained at a pressure slightly in excess of the test pressure. Valves 23 and 24 were kept closed so as to isolate the nitrogen from the rest of the system. The remainder of the valves were kept open. The vessel 11 and capillary tube 12 were filled with the test oil.

The liquid filled parts of the system were pressurized by injecting water into the vessel 2, by actuating the piston pump 5, and brought to the desired pressure. Valve 23 was opened to connect the nitrogen to the system. The system pressure was brought to the desired value by opening the bleed valve 24. The oven 26 was heated to the desired temperature until thermal equilibrium was reached. Valves 19 and 27 were closed. The fluid pressure in vessel 2 was increased by about 5 psi by operating the pump 5. The value of this pressure increment was monitored by the pressure transducer 17. Valve 16 was opened to allow flow of the test fluid through the capillary tube 12. The transducer response was recorded on a chart recorder.

Figure 2:
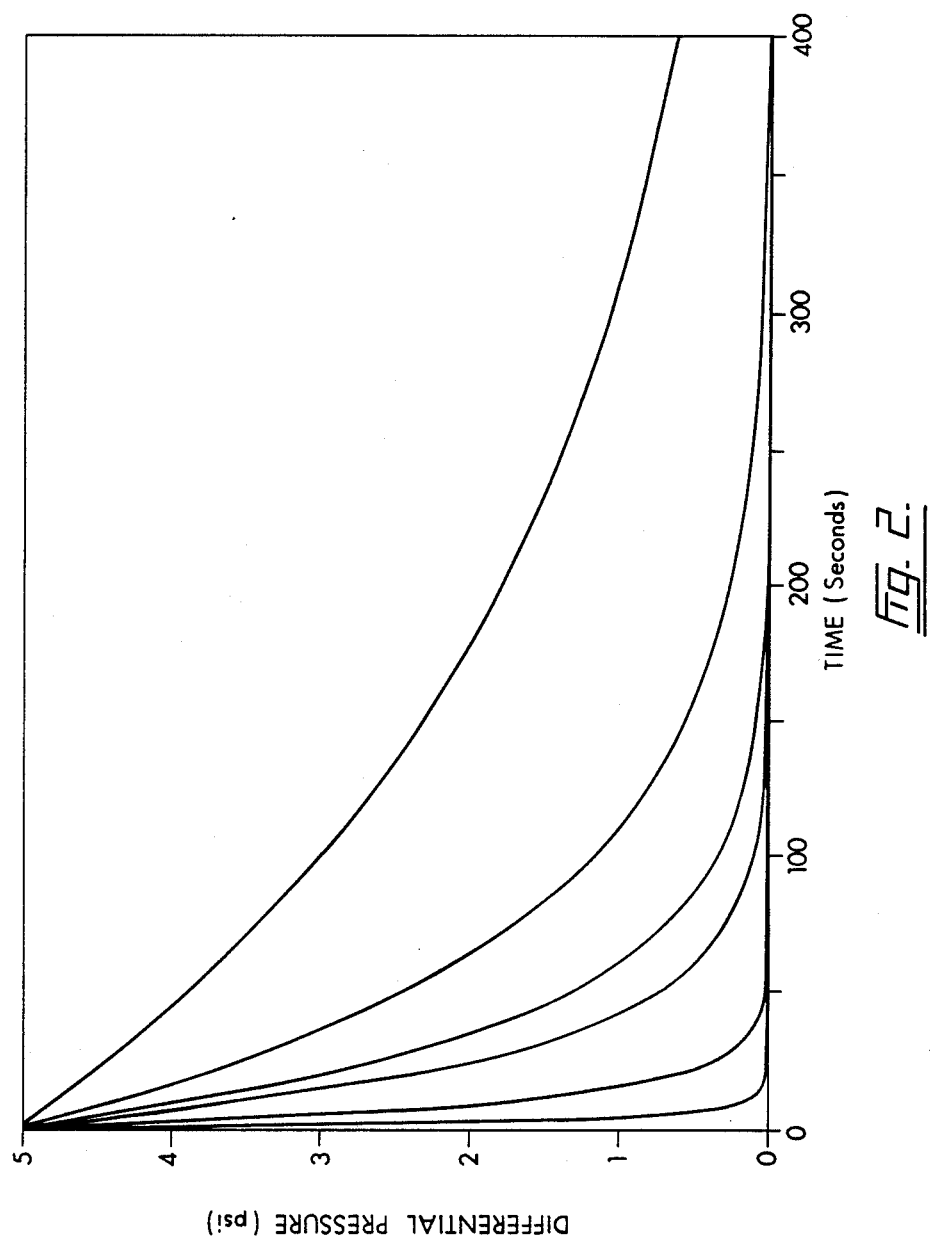
FIG. 2 is a plot of pressure differential versus time for six fluids of known viscosity.
Figure 3:
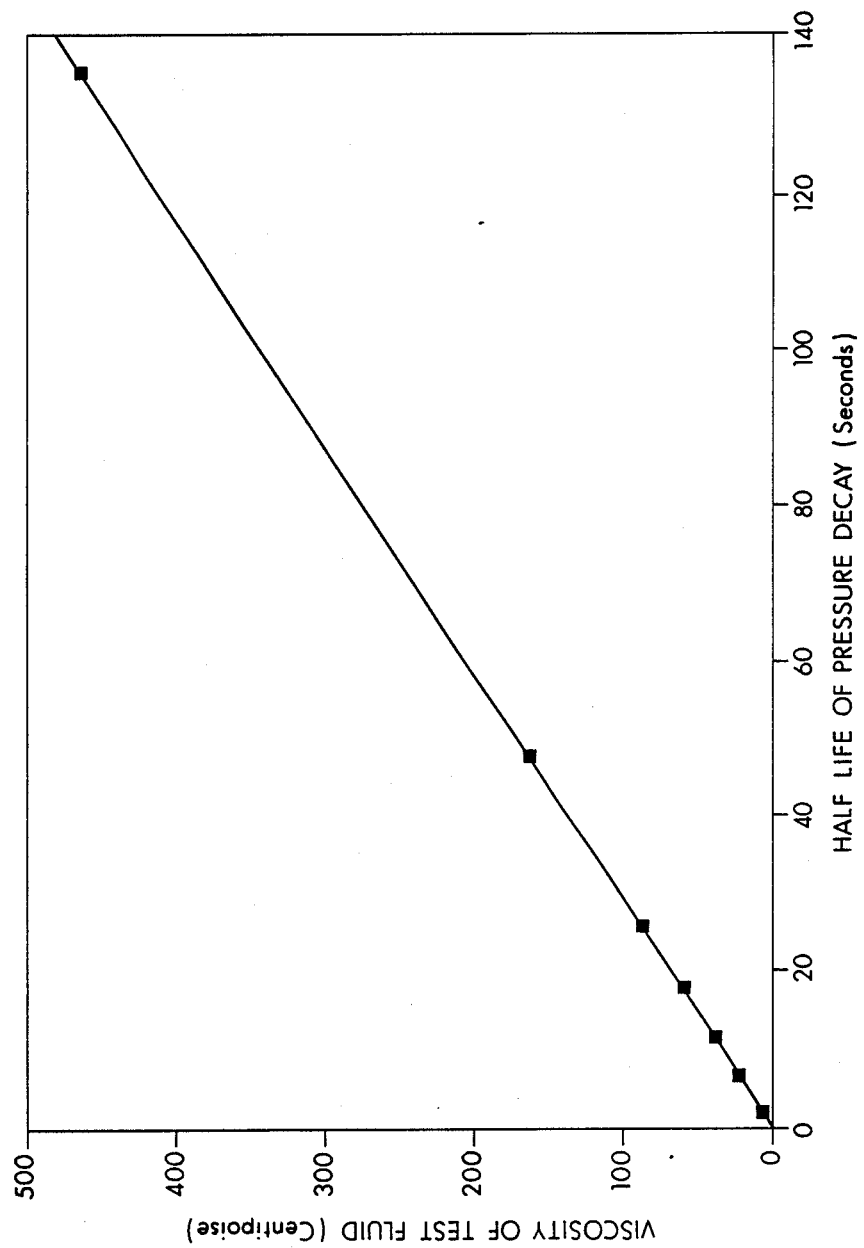
FIG. 3 is a graph showing the correlation between the viscosities of the test fluids used in the test shown in FIG. 3 versus the half-life of pressure decay calculated from the results of FIG. 2.

FIG. 2 shows recorded plots of pressure differential versus time obtained in accordance with the test procedure for 6 fluids of known viscosity. These plots were used to calculate, using the formulas provided hereinabove, the values of half life of pressure decay corresponding to each value of viscosity. FIG. 3 shows the observed relationship between half life and viscosity, and confirms that the half life of pressure decay is directly proportional to the viscosity of the fluid.

Figure 4:
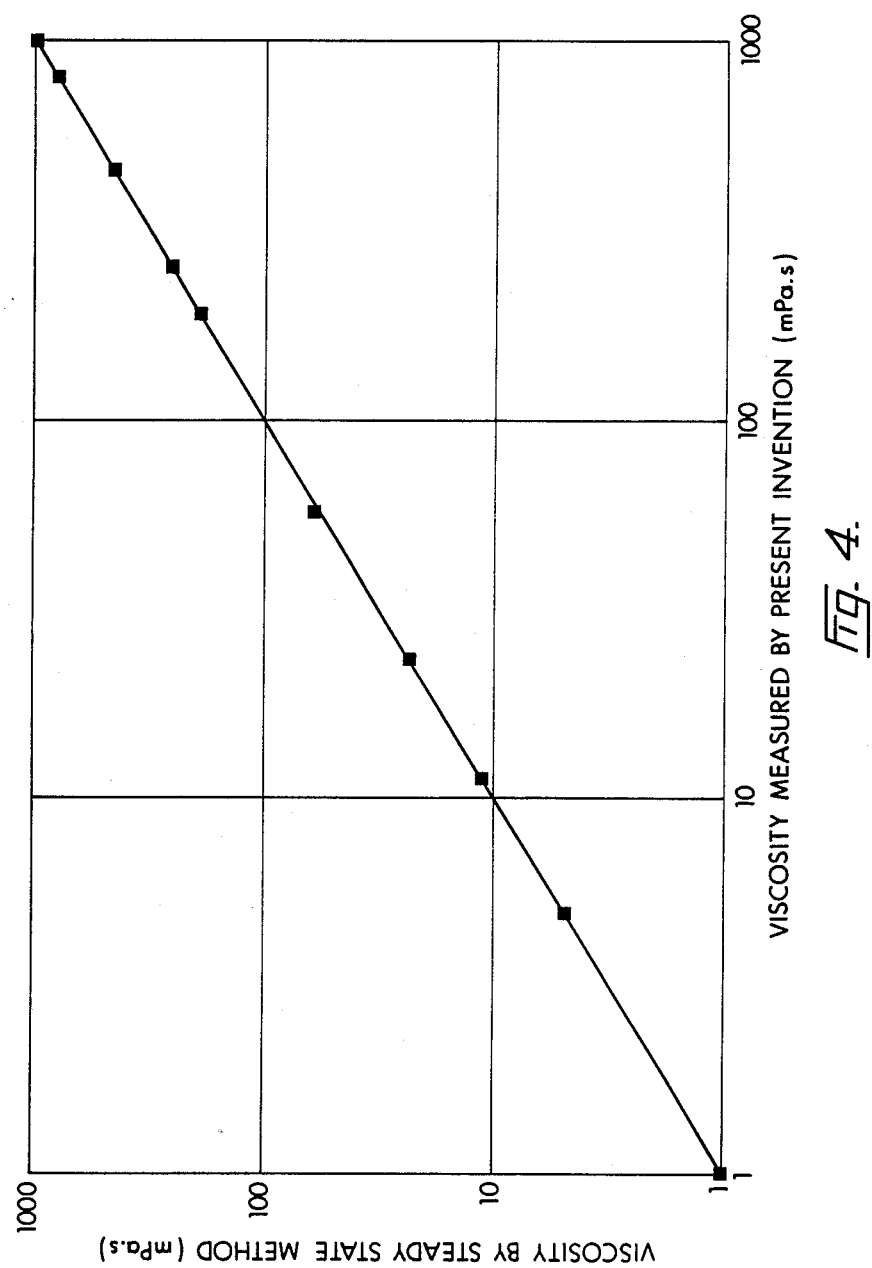
FIG. 4 shows a plot of viscosity values for various fluids using the embodiment of FIG. 1 versus viscosity values measured using a steady state capillary viscometer.

FIG. 4 shows a plot of viscosity values obtained by the test procedure for several fluids measured using the present viscometer versus viscosity values measured with a capillary viscometer under steady-state flow conditions. It is apparent that the two techniques provide essentially the same values of viscosity over a wide range of viscosities.

Figure 5:
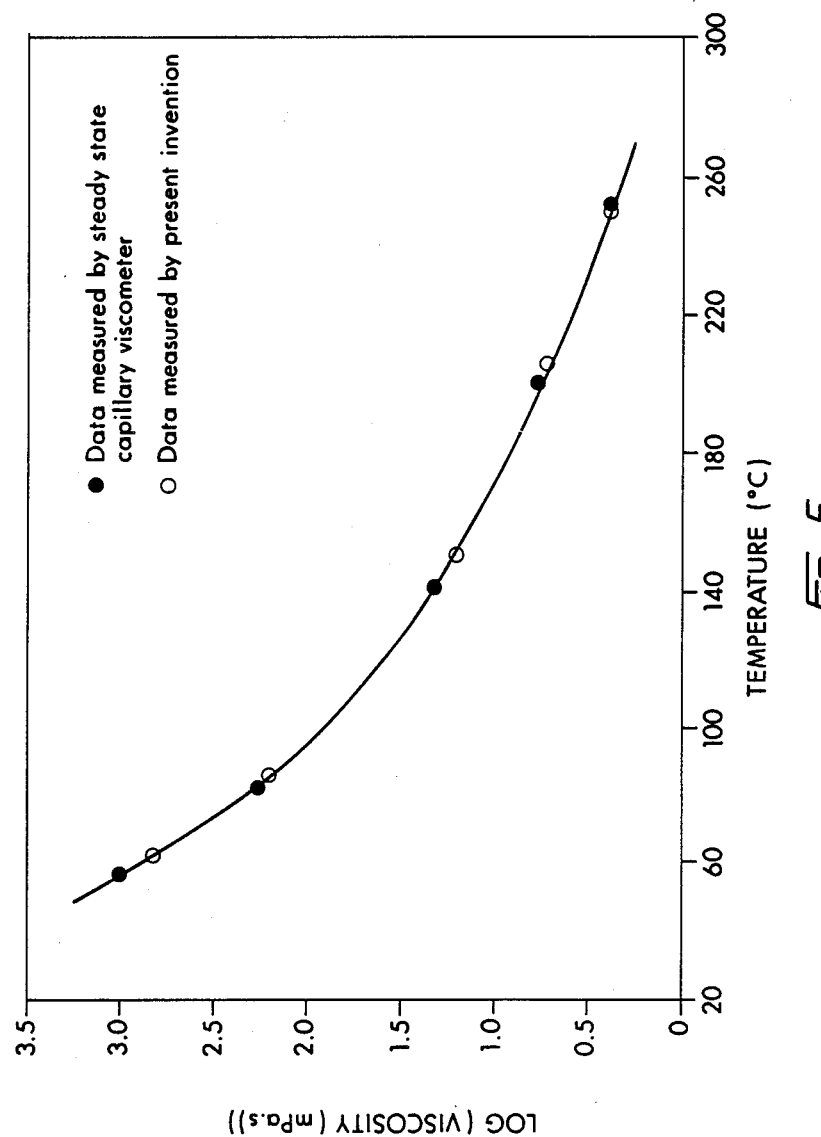
FIG. 5 is a plot of viscometer versus temperature for a heavy crude oil. The data measured by the viscometer of the present invention (shown as open circles) required only 10 cc of oil sample. The measurements were complete in 6 hours. The data measured with a steady-state viscometer (shown as blocked circles) required more than 1 liter of sample and took more than two days to complete.

FIG. 5 is a plot of viscosity versus temperature for a heavy crude oil. The points shown as open circles were obtained by applying the present invention. Only 10 cc of the oil sample was needed to obtain the complete viscosity versus temperature curve, and the series of measurements shown were completed within a time period of 6 hours. Points shown as solid circles were obtained with a steady-state viscometer. These required more than 1 liter of oils ample and more than two days to complete.

Reasonable variations and modifications which will become apparent to one skilled in the art can be made in this invention without departing from the spirit and scope thereof. For example, a back pressure regulator can be substituted in place of pressure vessel 21 to maintain constant pressure on the downstream side of the capillary tube 12. Bellows or flexible diaphragms can be incorporated into vessels 11 and 14 to prevent direct contact between the test fluid and the fluid contained in the rest of the system. It is also possible to use the test fluid to fill the entire system provided its compressibility is known or can be measured.

The embodiments of the invention in which an exclusive property or privilege is claimed are defined as follows:

1. A transient flow capillary viscometer for establishing a measure of the viscosity of a test fluid comprising:
   a capillary tube having upstream and downstream ends;
   first means, communicating with the downstream end of the capillary tube, for receiving fluid exiting the capillary tube and maintaining a substantially constant elevated pressure at said end;
   second means, communicating with the upstream end of the capillary tube, for maintaining the tube filled with test fluid during testing and inducing, in a pulsed manner, a pressure differential across the tube whereby test fluid may be caused to flow therethrough at a diminishing rate under a diminishing pressure differential; and
   third means for monitoring the thus generated diminishing pressure differential as a function of time to obtain information which may be used to calculate a measure indicative of the viscosity of the test fluid.

2. The viscometer as set forth in claim 1 wherein said second means comprises:
   a first pressure vessel adapted to be filled with a slightly compressible liquid;
   fourth means, connected with the first pressure vessel, for compressing the liquid therein;
   first conduit means connecting the first pressure vessel with the upstream end of the capillary tube, said conduit means including a second pressure vessel, smaller in size than the first pressure vessel, for containing a reservoir of test fluid for supply to the capillary tube to keep the latter filled with test fluid; and
   valve means, positioned in the first conduit means between the first pressure vessel and the second pressure vessel, for controlling the flow of liquid and the application of pressure from the first pressure vessel to the capillary tube.

3. The viscometer as set forth in claim 2 wherein said first means comprises:
   a third pressure vessel for containing a compressed gas; and
   second conduit means connecting the third pressure vessel with the downstream end of the capillary tube.

4. The viscometer as set forth in claim 3 comprising:
   means for heating the capillary tube and the second pressure vessel, whereby the test fluid may be heated and tested at different elevated temperatures.

5. A method for determining a measure indicative of the viscosity of a test fluid, comprising:
   providing a capillary tube filled with test fluid and means for keeping the capillary tube filled with test fluid during testing;
   maintaining a substantially constant elevated pressure at the downstream end of the capillary tube while enabling test fluid to exit from the downstream end of the capillary tube;
   applying, at the upstream end of the capillary tube, a pulse of pressure greater than the downstream end pressure to thereby induce a pressure differential across the capillary tube and cause the test fluid to flow through the capillary tube at a diminishing rate under a diminishing pressure differential; and
   monitoring the diminishing pressure differential across the capillary tube as a function of time to thereby obtain information which may be used to calculate a measure indicative of the viscosity of the test fluid.

6. A method for determining a measure indicative of the viscosity of a test fluid comprising:
   providing a first pressure vessel filled with a slightly compressible liquid, a capillary tube filled with test fluid, conduit means connecting the first pressure vessel and the upstream end of the capillary tube and adapted to keep the capillary tube filled with test fluid during testing, a valve controlling the conduit means whereby the first pressure vessel is isolated from the upstream end of the capillary tube when the valve is closed and is in communication with said upstream end of the capillary tube when open, and a third pressure vessel connected by a conduit with the downstream end of the capillary tube, said third pressure vessel and conduit containing pressurized gas and being adapted to receive fluid exiting the capillary tube and to maintain a substantially constant elevated pressure at the downstream end of the capillary tube;
   compressing the liquid in the first pressure vessel, with the valve closed, to a pressure greater than the pressure in the third vessel and then opening the valve to thereby induce a pressure differential in a pulsed manner across the capillary tube and cause the test fluid to flow through the capillary tube at a diminishing rate under a diminishing pressure differential; and
   monitoring the diminishing pressure differential across the capillary tube as a function of time; and
   calculating the half-life of pressure decay to obtain a measure indicative of the viscosity of the test fluid.

* * * * *